US011471554B2

(12) United States Patent
Muthuramalingam et al.

(10) Patent No.: US 11,471,554 B2
(45) Date of Patent: Oct. 18, 2022

(54) AIR PURIFIER AND AUTOMOBILE AIR CONDITIONER WITH AIR PURIFIER

(71) Applicant: Industrial Technology Research Institute, Hsinchu (TW)

(72) Inventors: Karthickraj Muthuramalingam, Hsinchu (TW); Chen-Peng Hsu, Hsinchu (TW); Chien-Chun Lu, New Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 541 days.

(21) Appl. No.: 16/525,616

(22) Filed: Jul. 30, 2019

(65) Prior Publication Data

US 2021/0030914 A1 Feb. 4, 2021

(51) Int. Cl.
*A61L 9/20* (2006.01)
*B01D 53/86* (2006.01)

(52) U.S. Cl.
CPC .......... *A61L 9/205* (2013.01); *B01D 53/8687* (2013.01); *A61L 2209/12* (2013.01); *A61L 2209/16* (2013.01); *B01D 2255/2094* (2013.01); *B01D 2255/20707* (2013.01); *B01D 2255/20723* (2013.01); *B01D 2255/20738* (2013.01); *B01D 2255/20769* (2013.01); *B01D 2255/20776* (2013.01); *B01D 2255/20792* (2013.01); *B01D 2255/802* (2013.01)

(58) Field of Classification Search
None
See application file for complete search history.

(56) References Cited

U.S. PATENT DOCUMENTS

| | | | |
|---|---|---|---|
| 8,048,391 | B2 | 11/2011 | Molins |
| 8,409,338 | B2 | 4/2013 | Kim et al. |
| 9,999,782 | B2 | 6/2018 | Shur et al. |
| 10,046,070 | B1 | 8/2018 | Zaborsky et al. |
| 2011/0142725 | A1 | 6/2011 | Liu et al. |
| 2013/0034470 | A1 | 2/2013 | Wang et al. |
| 2013/0313104 | A1 | 11/2013 | Yates et al. |

(Continued)

FOREIGN PATENT DOCUMENTS

| | | |
|---|---|---|
| CN | 204611988 | 9/2015 |
| CN | 208741551 | 4/2019 |

(Continued)

OTHER PUBLICATIONS

"Notice of Allowance of Taiwan Counterpart Application," dated Dec. 7, 2020, p. 1-p. 3, in which the listed reference was/references were cited.

*Primary Examiner* — Jelitza M Perez
(74) *Attorney, Agent, or Firm* — JCIPRNET

(57) ABSTRACT

The disclosure is directed to an air purifier and an automobile air conditioner with an air purifier. The air purifier includes a reactor, a column, an air guider and a plurality of light emitting elements. The reactor includes an air inlet and an air outlet. The column is disposed in the reactor, and the column has a N-side walls. The air guider is disposed on the column, and the air guider is coated with a photocatalyst. The light emitting elements are placed on the N side walls of the column configured to irradiate on the photocatalyst, where each of the light emitting elements has an emitting angle of $\theta$ and $\theta*N>360°$.

20 Claims, 13 Drawing Sheets

(56) References Cited

U.S. PATENT DOCUMENTS

| | | | | |
|---|---|---|---|---|
| 2014/0227140 | A1* | 8/2014 | Engelhard | A61L 9/20 422/121 |
| 2017/0245527 | A1 | 8/2017 | Dobrinsky et al. | |
| 2019/0240370 | A1* | 8/2019 | Benedek | A61L 9/122 |

FOREIGN PATENT DOCUMENTS

| | | |
|---|---|---|
| CN | 208871762 | 5/2019 |
| TW | 201511522 | 3/2015 |
| TW | 201542992 | 11/2015 |

* cited by examiner

000# AIR PURIFIER AND AUTOMOBILE AIR CONDITIONER WITH AIR PURIFIER

TECHNICAL FIELD

The disclosure is related to an air purifier and an automobile air conditioner with an air purifier, which uses a photocatalytic air purification method by using ultraviolet (UV) lights.

BACKGROUND

Generally, an air purifier is used to remove microorganism and other pollutants from air, by performing an air purification process. To perform the air purification process, the air is allowed to pass through the air purifier to filter out the microorganisms and other pollutants from the air. Primarily, the air purifier with a filter is used to remove a dust and other pollutants presented in the air. However, the filter may remove the dust and the other pollutants but the microorganism, volatile organic compounds (VOCs) and/or a biological contaminant, generally referred as VOCs, will pass through the filter during the air purification process performed by the air purifier.

SUMMARY

Accordingly, the disclosure is directed to an air purifier and an automobile air conditioner with an air purifier.

In one aspect, the disclosure is directed to an air purifier which includes a reactor, a column, an air guider and a plurality of light emitting elements. The reactor includes an air inlet and an air outlet. The column is disposed in the reactor, and the column has N-side walls. The air guider is disposed on the column, and the air guider is coated with a photocatalyst. The plurality of light emitting elements are placed on the N side walls of the column. Each of the light emitting elements has an emitting angle of $\theta$ and $\theta*N>360°$.

In one aspect, the disclosure is directed to an automobile air conditioner which includes a vent chamber. The vent chamber includes an air inlet and an air outlet, and further includes a reactor, a column, an air guider and a plurality of light emitting elements. The reactor is configured to purify air in the automobile air conditioner. The column is disposed in the reactor, and the column has a N-side walls. The air guider is disposed on the column, and the air guider is coated with a photocatalyst. The plurality of light emitting elements are placed on the N side walls of the column. Each of light emitting elements has an emitting angle of $\theta$ and $\theta*N>360°$.

In one aspect, the disclosure is directed to an air purifier which includes a reactor, a plurality of columns, an air guider and a plurality of light emitting elements. The reactor which includes an air inlet and an air outlet. The plurality of columns are disposed in the reactor, where each of the plurality of columns has N side walls. The air guider is disposed on each of the plurality of the columns, and the air guider is coated with a photocatalyst. The light emitting elements are placed on the N side walls of the plurality of columns. Each of the light emitting elements has an emitting angle of $\theta$ and $\theta*N>360°$.

In order to make the aforementioned features and advantages of the disclosure comprehensible, exemplary embodiments accompanied with figures are described in detail below. It is to be understood that both the foregoing general description and the following detailed description are exemplary, and are intended to provide further explanation of the disclosure as claimed.

It should be understood, however, that this summary may not contain all of the aspect and embodiments of the disclosure and is therefore not meant to be limiting or restrictive in any manner. Also, the disclosure would include improvements and modifications which are obvious to one skilled in the art.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION OF DISCLOSED EMBODIMENTS

Figure 1:
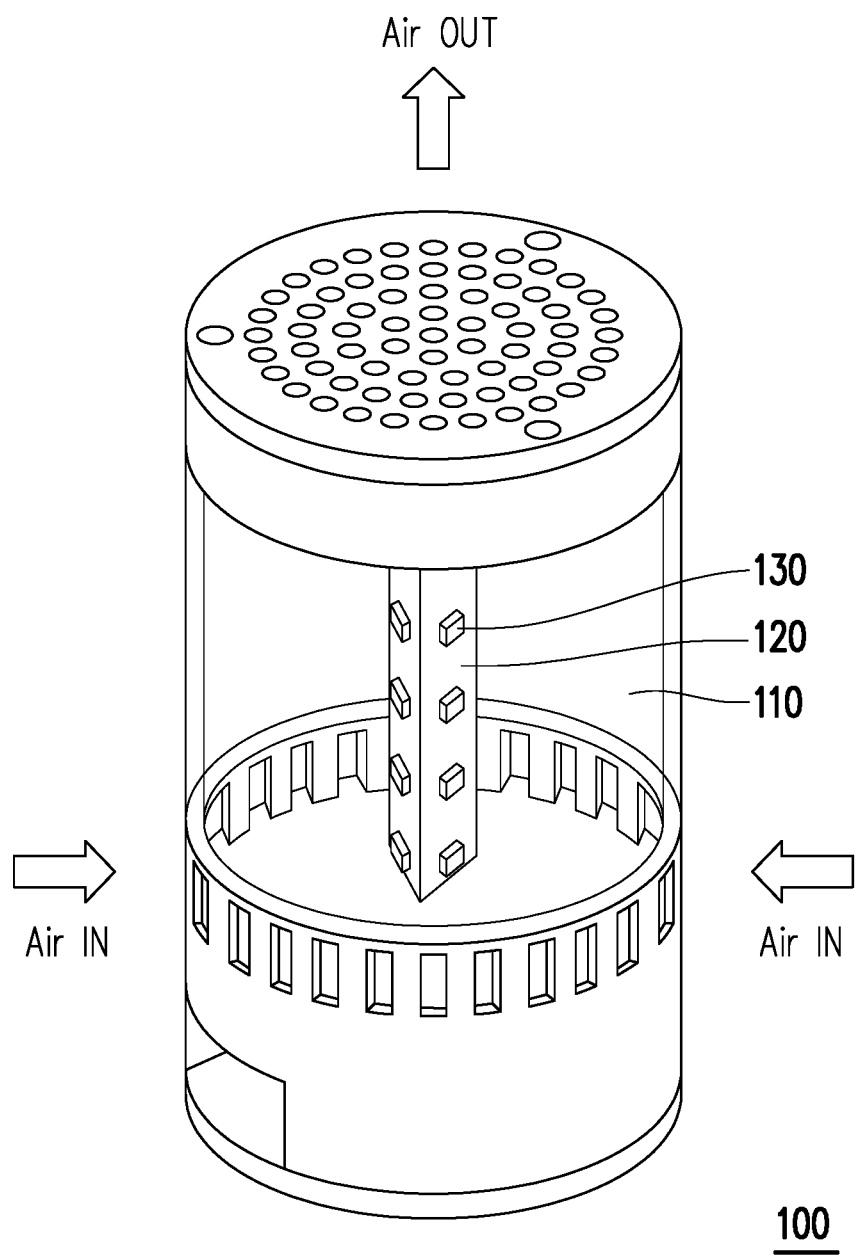
FIG. 1 illustrates an air purifier according to an embodiment of the disclosure.

Reference will now be made in detail to the present exemplary embodiments of the disclosure, examples of which are illustrated in the accompanying drawings. Wherever possible, the same reference numbers are used in the drawings and the description to refer to the same or like parts.

The disclosure is directed to an air purifier and an automobile air conditioner with an air purifier.

Considering volatile organic compounds (VOCs) and/or a biological contaminant, in the air after air purification, and to filter out the VOCs, the air purifier uses a photocatalytic oxidation (PCO) method to purify the air. The photocatalytic oxidation method is achieved by adopting a light emitting element in the air purifier. The light emitting element uses in the photocatalytic oxidation may be an ultraviolet light (UV) emitting element, and/or an infrared (IR) light emitting element, which may irradiate a photocatalyst during the air purification process, and producing hydroxyl radicals and super-oxide ions that may react with the VOCs to turn them into carbon dioxide and water.

Challenges associated with a total illuminating area of the light emitting element in the air purifier is a target for any purifier. On the other hand, achieving the total illumination area by using a lot of light emitting elements may result in increasing the energy consumption in the air purifier. In addition, residence time of the air with the VOCs during the air purification process in the air purifier is subjected to investigate. When the air flows into the air purifier during the air purification process for multiple times in order to effectively remove the VOCs in the air, and it consumes more time than expected during air purification.

Thus, the air purifier needs to filter out the VOCs effectively by increasing number of the light emitting elements to perform photocatalytic oxidation.

In another aspect, increase residence time of the air with the VOCs during air purification process in the air purifier is target for any air purifier.

FIG. 1 schematically shows an air purifier according to an embodiment of the disclosure. Referring to FIG. 1, an air purifier 100 of the embodiment includes a reactor 110, a column 120 and a plurality of light emitting elements 130.

The reactor 110 is a container, where photocatalytic oxidation takes place during air purification process. The reactor 110 has an air inlet (Air IN) at one end of the reactor 110, and an air outlet (Air OUT) at the other end of the reactor 110.

In the reactor 110, air flows into the air purifier 100 through the air inlet (Air IN) to perform air purification process and purified air is obtain by the air outlet (Air OUT).

The inner sidewall of the reactor 110 is made of a solid material which may be a transparent or a non-transparent, thus the type of material for the sidewall of the reactor 110 is not limited in the disclosure. The inner sidewall of the reactor 110 may be coated with a catalyst.

The column 120 is a light emitting element holder for holding the light emitting elements 130 in the reactor 110. The column 120 is disposed in the reactor 110 has N side walls, the value of N may determine to increase the number of light emitting elements 130 disposed on the N side walls of the column 120. The column 120 is a solid material and/or a transparent glass, thus the type of material for the column 120 is not limited in this disclosure.

The light emitting elements 130 is an ultraviolent (UV) lights, a visible lights and/or other light emitting elements used for photocatalytic oxidation; thus, the type of the light emitting elements 130 in the air purifier 100 is not limited in the disclosure.

The light emitting elements 130 disposed on the column 120 are used for the photocatalytic oxidation process in the air purifier 100. The light emitting elements 130 may irradiate the light on the photocatalyst coated on the inner sidewall of the reactor 110 during air purification process in the air purifier 100.

The photocatalyst may be titanium dioxide, zinc oxide, ferric oxide, cadmium sulfide, cadmium selenide, tungsten trioxide, molybdenum trioxide, vanadium pentoxide, tin oxide, and/or combinations of the different photocatalyst, thus the photocatalyst material is not limited in this disclosure. The presence of photocatalyst in the air purifier 100 for photocatalytic oxidation may be presented in the side walls of the reactor 110, the column 120 and/or other parts of the air purifier 100, thus the photocatalyst in the air purifier 100 is not limited herein.

The method of coating the photocatalyst in the air purifier 100 is not limited as it may be applied in the form of a powder and/or a film.

The method of coating the photocatalyst includes sol-gel, liquid vapor deposition, chemical vapor deposition, thermal decomposition, magnetron sputtering, dip coating, and/or spraying, and the examples are not limited in the disclosure.

Figure 2:
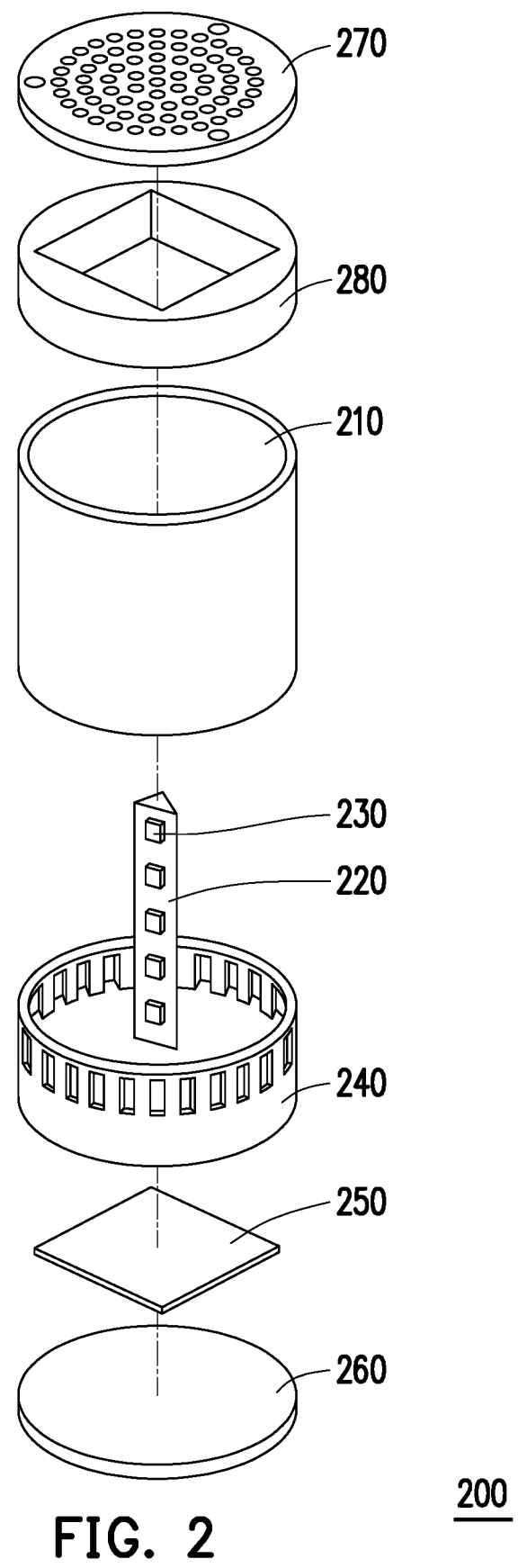
FIG. 2 illustrates an exploded view of an air purifier according to an embodiment of the disclosure.

FIG. 2 schematically shows an exploded view of an air purifier according to an embodiment of the disclosure. The air purifier 200 includes a reactor 210, a column 220, a plurality of light emitting elements 230, a bottom housing 240, a controller 250, a bottom cover 260, a top cover 270, and a fan holder 280. The reactor 210, the column 220, and the light emitting elements 230 respectively similar to a reactor 110, a column 120 and a plurality of light emitting elements 130 with reference to FIG. 1, thus the detail description of structure and operations of the reactor 210, the column 220, and the light emitting elements 230 are omitted herein.

The bottom housing 240 works as a housing for an air inlet (Air IN) of the air purifier 200, and the top cover 270 works as an air outlet (Air OUT) in the air purifier 200. The air inlet (Air IN) allows air flows into the air purifier 200 to perform air purification process and obtains purified air at the top cover 270.

The bottom housing 240 is a solid material and/or a transparent glass, thus the type of material used for bottom housing 240 is not limited in this disclosure.

The controller 250 is an electronic circuit board/printed circuit board (PCB) in the air purifier 200. The controller 250 is used to control the illumination intensity of the light emitting elements 230 disposed on the column 220.

In one embodiment, a fan, which is not shown in FIG. 2 is placed near the air outlet (Air OUT) of the top cover 270 to force the air to flow out the reactor 110.

The column 220 is used for holding the light emitting elements 230 in the reactor 210. The column 220 is disposed in the reactor 210 has N side walls, the value of N may determine to increase the number of light emitting elements 220 disposed on the N side walls of the column 220.

Figure 3B:
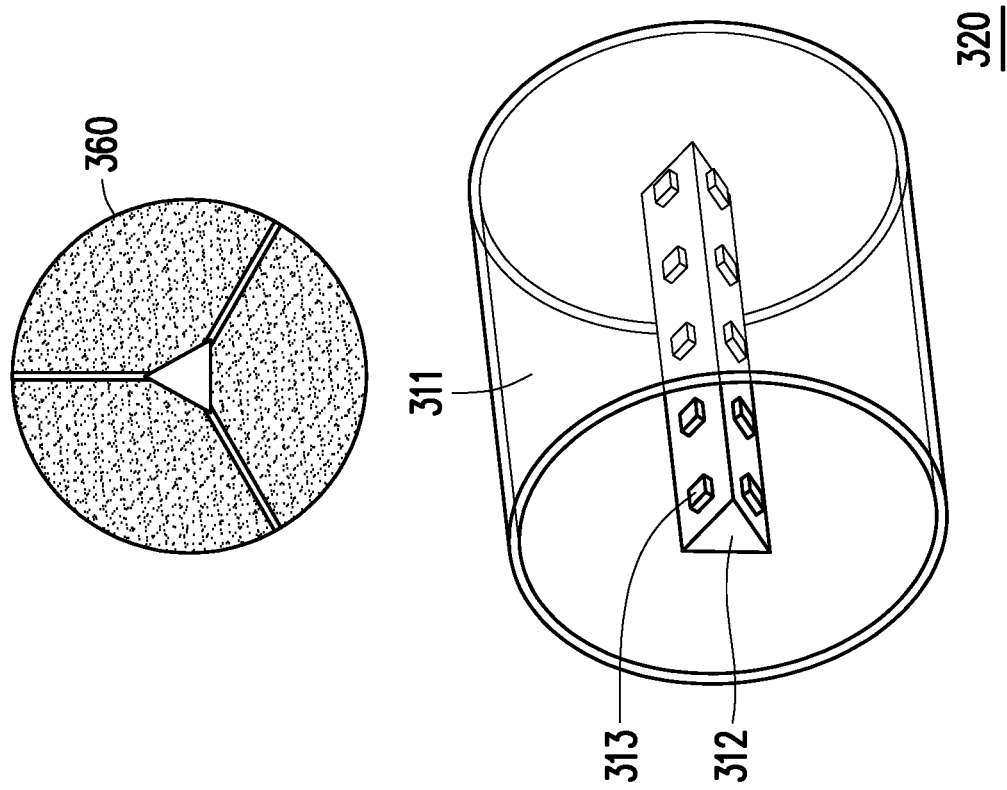
FIGS. 3A, 3B and 3C respectively illustrate different types of a column in an air purifier according to an embodiment of the disclosure.
Figure 3A:
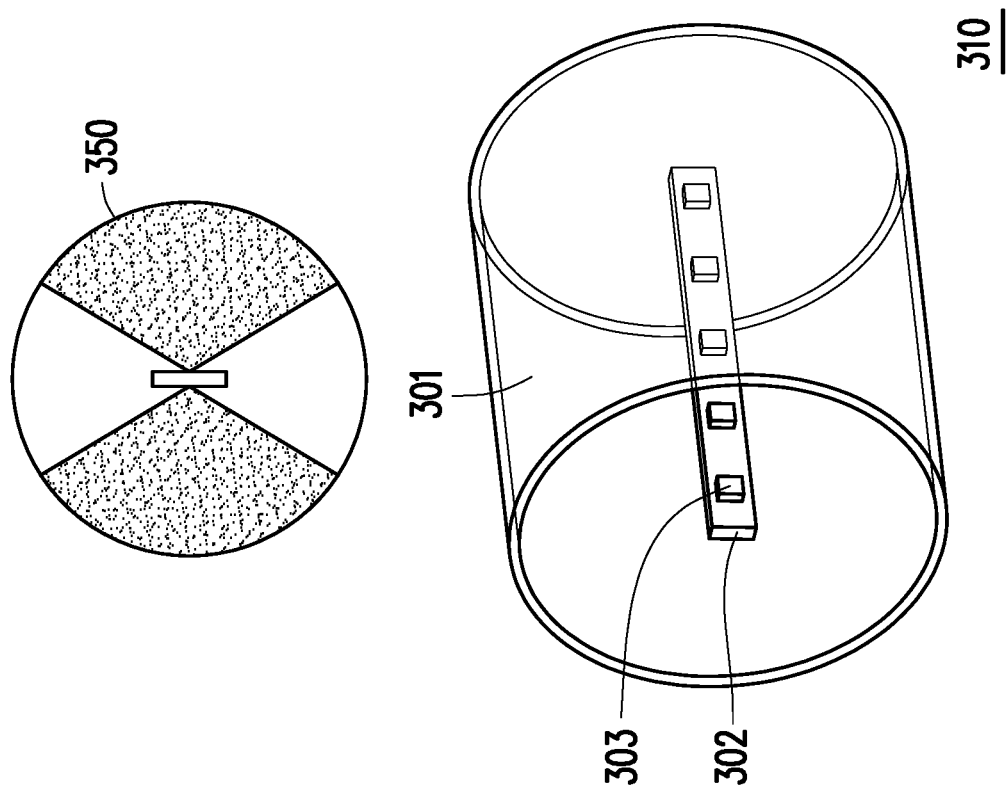
Figure 3C:
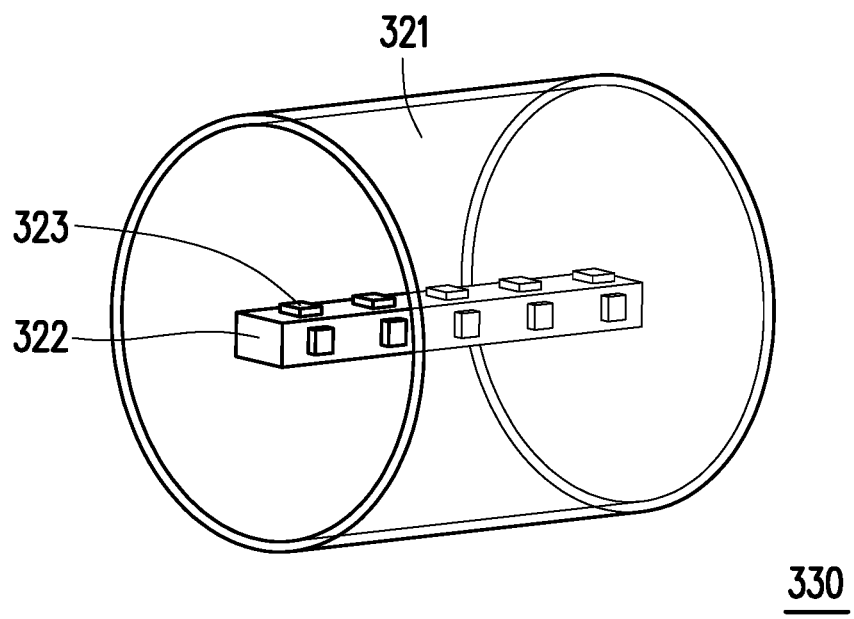

FIGS. 3A, 3B and 3C respectively illustrate different types of a column in an air purifier according to an embodiment of the disclosure. The air purifier (310, 320, 330) includes a reactor (301, 311, 321), a column (302, 312, 322) and a plurality of light emitting elements (303, 313, 323). The reactor (301, 311, 321), the column (302, 312, 322), and the light emitting elements (303, 313, 323) are respectively similar to a reactor 110, a column 120 and a plurality of light emitting elements 130 with reference to FIG.

1, thus the detailed description of structure and operations of the reactor (301, 311, 321), the column (302, 312, 322), and the light emitting elements (303, 313, 323) are omitted herein.

Referring to FIG. 3A, the air purifier 310 includes the column 302 and the light emitting elements 303.

The column 302 is used for holding the light emitting elements 303 in the reactor 301. The column 302 is disposed in the reactor 301 has N side walls, the value of N may be 2 in this embodiment. By determining the number of side walls is 2, the column 302 is in a rectangular shape. In detail, the light emitting elements 303 are disposed on the either side of the column 302. Each of the light emitting elements 303 emit light with an emitting angle of $\theta$. Each of the light emitting elements 303 disposed on the column 302 emit light with an emitting angle $\theta=120°$. The emitting angle of the light emitting elements 303 in the column 302 with 2 side walls is determined as $\theta*2<360°$. In detail, a total illuminating angle of the light emitting elements 303 is the product of emitting angle $\theta$ of each of the light emitting elements and the 2 side walls of the column. The total illuminating angle of the light emitting elements 303 is less than 360 degrees.

The photocatalyst surface area Ac of the air purifier 310 is calculated as Ac=H*D(L+R), wherein L is the length of the reactor of the purifier 310 and R is the diameter of the reactor of the purifier 310.

Based on the above predetermined values, the total illuminated area ($A_{ILL}$) in the air purifier 310 is calculated as, $$A_{ILL} = \{1-(360°-N*\theta)\}*A_C \quad (1)$$

Based on the above expression (1), for the column 302 with 2 side walls, the total illuminated area is calculated as $A_{ILL}=\frac{1}{3}A_c$, shows that the photocatalyst surface area 350 are not fully illuminated by the light emitting elements 303 in the air purifier 310.

It is noted that the emitting angle θ of light emitting elements 303 is not limited to be 120°.

In some embodiments, the light emitting elements 303 in the air purifier 310 may use same θ.

In some embodiments, the light emitting elements 303 in the air purifier 310 may use different θ. In detail, each of the light emitting elements 303 in the air purifier 310 have different θ. Thus, the emitting angle θ of the light emitting elements 303 used in the air purifier 310 is not limited in this disclosure.

With reference to FIG. 3B, the air purifier 320 includes the column 312 and the light emitting elements 313.

The column 312 is used for holding the light emitting elements 313 in the reactor 311. The column 312 is disposed in the reactor 311 has N side walls, the value of N may be 3 in this embodiment. By determining the N side walls is 3, the top surface of column 312 view from one end is in a triangle shape. In detail, the light emitting elements 313 are disposed on each side of triangle in the column 312.

Each of the light emitting elements 313 emit light with an emitting angle of θ. Each of the light emitting elements 313 disposed on the column 312 emit light with an emitting angle θ=120°. The emitting angle of the light emitting elements 313 in the column 312 with 3 side walls is determined as θ*3=360°. In detail, a total illuminating angle of the light emitting elements 313 is the product of emitting angle θ of each of the light emitting elements and the N side walls of the column. The total illuminating angle of the light emitting elements 313 is equal to 360 degrees.

The photocatalyst surface area Ac of the air purifier 320 is calculated as Ac=H*D(L+R).

Based on the above predetermined values, by using expression (1), the total illuminated area of the column 312 with 3 side walls is calculated as, $A_{ILL}=A_c$, shows that the photocatalyst surface area 360 are fully illuminated by the light emitting elements 313 disposed on the column 312 with 3 sides in the air purifier 320.

Based on the above, the emitting angle of the light emitting elements 313 disposed on the column 312 with 3 side walls is determined as θ*3=360°, so that the air purifier 320 is fully illuminated during air purification.

Referring to FIG. 3C, the air purifier 330 includes the column 322 and the light emitting elements 323.

The column 322 is used for holding the light emitting elements 323 in the reactor 321. The column 322 is disposed in the reactor 311 has N side walls, the value of N may be 4 in this embodiment. By determining the N side walls is 4, the top surface of column 322 view from one end is in a square shape. In detail, the light emitting elements 323 are disposed on each side of square in the column 322.

Each of the light emitting elements 323 emit light with an emitting angle of θ. Each of the light emitting elements 313 disposed on the column 312 emit light with an emitting angle θ=120°. The emitting angle of the light emitting elements 323 in the column 322 with 4 side walls is determined as θ*4>360°. In detail, a total illuminating angle of the light emitting elements 323 is the product of emitting angle θ of each of the light emitting elements and the N side walls of the column. The total illuminating angle of the light emitting elements 323 is greater than 360 degrees.

With reference to FIG. 3A, 3B and 3C, by choosing the emitting angle of the light emitting elements to be 120°, the product of emitting angle θ and the N side walls of the column will equal or exceed 360° when the N value greater than or equal to 3. Therefore, the photocatalyst surface area can be fully illuminated by the light emitting elements disposed on the column in the air purifier.

Based on the above, the number of side walls in the column (312, 322) is at least 3 to increase the number of light emitting elements (313, 323) in the air purifier (320, 330), thereby increasing efficiency of the photocatalytic oxidation during air purification process.

In some embodiments, the column may have hexagonal shape and the N value is 6. In some embodiments, the column may have pentagonal shape and the N value is 5. Thus, the shape of the column in this disclosure is not limited thereto. In some embodiments, the arrangements of the light emitting elements can be pentagonal shape from one end of the column. The arrangements of the light emitting elements can be hexagonal shape from one end of the column. Thus, the arrangement of the light emitting elements in the air purifier is not limited in the disclosure.

Figure 4A:
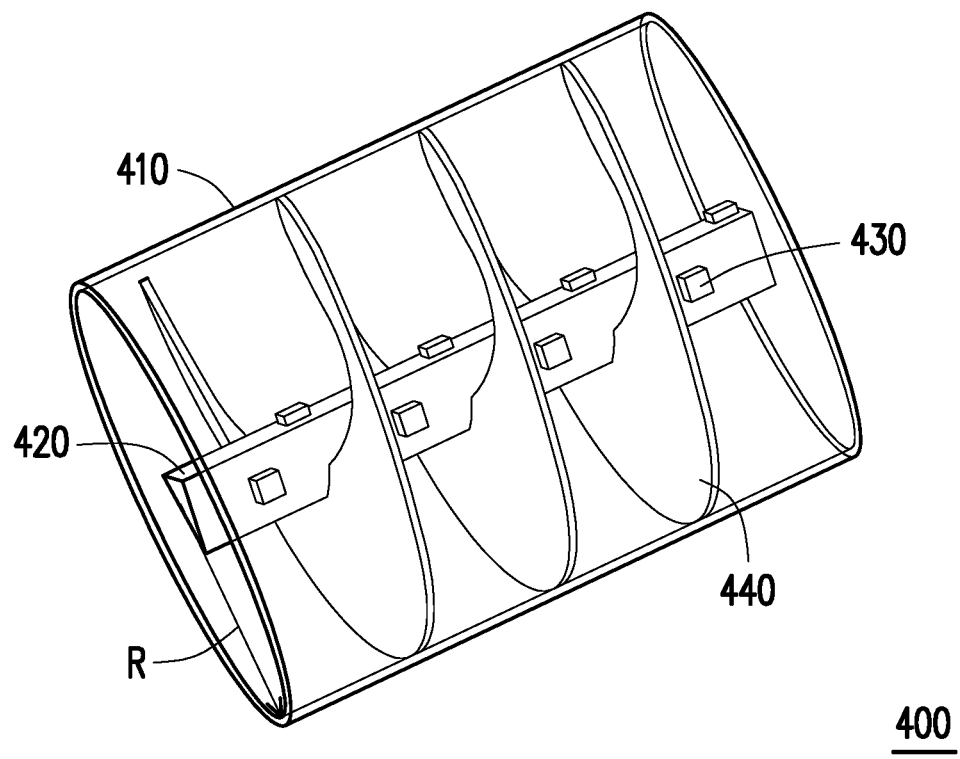
FIG. 4A illustrates an air purifier according to an embodiment of the disclosure.
Figure 4B:
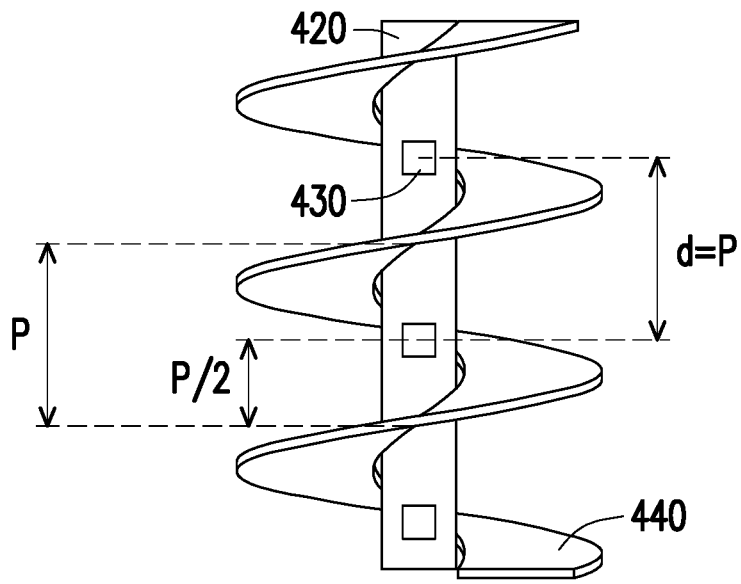
FIG. 4B illustrates an air guider in an air purifier according to an exemplary embodiment of the disclosure.

FIG. 4A schematically shows an air purifier according to an embodiment of the disclosure. FIG. 4B schematically shows the air guider in the air purifier according to the embodiment of FIG. 4A. The air purifier 400 includes a reactor 410, a column 420, a plurality of light emitting elements 430 and an air guider 440. The reactor 410, the column 420 and the light emitting elements 430 are respectively similar to a reactor 110, a column 120 and a plurality of light emitting elements 130 with reference to FIG. 1, thus the detailed description of structure and operations of the reactor 410, the column 420 and the light emitting elements 430, are omitted herein.

The column 420 is used for holding the light emitting elements 430 in the reactor 410. The column 420 is disposed in the reactor 410 has N side walls. The inner sidewall of the reactor 410 is coated with a photocatalyst. The value N of the column 420 is chosen to be more than 3 or equal to 3 to increase the total illuminated area on the photocatalyst surface area.

The air guider 440 is disposed on the column 420. In some embodiments, the air guider 440 is fixed to the column 420.

In some embodiments, the air guider 440 is rotate along an axis of the column 420, thus the mechanical movement of the air guider 440 disposed on the column 420 is not limited in the disclosure. The mechanical movement of the column 420 is implemented by adding some additional circuits in the air purifier 400.

The air guider 440 may be a helical, a cylinder, a pentagonal, a hexagonal and/or disk shape. The shape of air guider 440 is determined by the design requirement, thus the shape of air guider 440 in the air purifier 400 is not limited in the disclosure. The air guider 440 is a solid material and/or a transparent glass, thus the type material for the air guider 440 is not limited herein.

The surface of the air guider 440 may be coated with the photocatalyst to further increase the photocatalyst surface area in the air purifier 400. The photocatalyst may be coated on the upward side surface of the air guider 440 or the downward side surface of the air guider 440. The photocatalyst may also be coated on either side surface or both side surface.

In some embodiments, the helical shape air guider 440 is preferred. The helical shape air guider 440 is used in the air purifier 400 is to increase residence time of the air with a VOCs during air purification process in the air purifier 400, thereby efficiency of air purification in the air purifier 400 is improved.

In one embodiment, the residence time of the air in the air purifier 400 during air purification without the air guider 440 is calculated as $$\text{Residence time } (t_r) = V_A * L \quad (2)$$

$V_A$ is the velocity of the air. L is the length of the reactor 410. D is the diameter of the reactor. The length of the reactor 410 is twice the diameter of the reactor. Therefore, L=2D. As such, the residence time $(t_r)$ is calculated as $t_r = 2V_A * D$.

It is noted that the residence time of the air purifier 400 depends on the velocity of the air $V_A$ and the length L of the reactor 410. By choosing the reactor 410 with different dimensions, the residence time $(t_r)$ of the air in the air purifier 400 is determined. Thus, the dimensions of the reactor 410 used in the air purifier 400 is not limited in this disclosure.

In one embodiment, by adopting air guider 440 with the helical shape in the air purifier 400, the length of the air guider 440 is calculated as $L_{AG} = 3\Pi D$.

Based on the above predetermined value, the residence time $(t_r)$ is calculated as $t_r = 3\Pi V_A * D$, The residence time $(t_r)$ of the air in the reactor 410 with the air guider 440 is 4.72 times larger than the residence time $(t_r)$ of the air in the reactor 410 without the air guider 440. Because of the air guider 440, the rout length of the air in the reactor 410 is increase from the length L of the reactor 410 to the length of the air guider 440. Therefore, the travel distance of the air is increased and the residence time $(t_r)$ is also increased.

Based on the above, the helical shape air guider 440 in the air purifier 400 increases the residence time $(t_r)$ of the air with the VOCs in the air purifier 400 during the air purification, thus efficiency of the air purifier 400 is improved.

In some embodiments, the residence time $(t_r)$ of the air in the reactor 410 is calculated based on the type of air guider used in the reactor 410.

Based on the above, the residence time $(t_r)$ of the air depends upon on the type of the reactor 410 and the air guider 440. By choosing reactor 410 with different dimensions and/or the different types of the air guider 440 in the air purifier 400, the residence time $(t_r)$ of the air in the air purifier 400 is varied. Thus, the type of the reactor 410 and the type of the air guider 440 used in the air purifier 400 to increase the residence time $(t_r)$ of the air is not limited in this disclosure.

In one embodiment, the distance (d) between the two adjacent light emitting elements 430 is equal to the pitch (P) or the period (P) (i.e., d=P) of the helical shape air guider 440 disposed on the column 420.

In one embodiment, the distance (d) between the two adjacent light emitting elements 430 to each side of the helical shaped air guider 440 is equal to half of the pitch (P) of the air guider (i.e., d/2=P/2). In other words, at least one side of the helical shape air guider 440 is presented between two adjacent light emitting elements 430 at an equal distance (i.e., P/2).

By choosing the helical shaped air guider 440, the number of rotations of the air guider 440 in the reactor 410 is increased, thereby increasing the residence time $(t_r)$ of the air in the air purifier 400.

By using air guider 440 in the air purifier 400, the residence time $(t_r)$ of air with a VOCs during an air purification process in the air purifier 400 is increased, thereby the improving efficiency of the air purifier 400.

Referring to FIGS. 4A and 4B, the radius of the reactor 410 is defined as R, which may be used to determine the number of light emitting elements 430 illuminating on the photocatalyst in the reactor 410 during photocatalytic oxidation.

In one embodiment, a ratio between d and R of the air purifier 400 is predetermined to be 3:5. For an example, if the radius of the reactor 410 is taken as 35 mm (i.e., R=35 mm), then the distance d between two adjacent light emitting elements 430 is 21 mm (i.e., d=21 mm), which gives the ratio of 3:5 to increase the number of light emitting elements 430 illuminating on the photocatalyst during the photocatalytic oxidation, thereby improving efficiency of the air purifier 400.

FIGS. 5A, 5B, 5C and 5D respectively illustrate the design structures of an air purifier according to an embodiment of the disclosure. The air purifier (510, 520, 530, 540) includes a reactor (511, 521, 531, 541), a column (514, 524, 534) and a plurality of light emitting elements (515, 525, 535, 545). The reactor (511, 521, 531, 541), the column (514, 524, 534) and the light emitting elements (515, 525, 535, 545) are respectively similar to the reactor 110, the column 120 and the light emitting elements 130 with reference to FIG. 1, thus the detailed description is omitted herein.

The reactor (511, 521, 531,541) includes an air inlet (513, 523, 533, 543) on the top end and an air outlet (512, 522, 532, 542) on sidewall of the reactor (511, 521, 531,541) near the bottom end. In the reactor, the air flows into the air purifier (510, 520, 530, 540) through the air inlet (513, 523, 533, 543) and performs air purification process and the purified air is obtained at the air outlet (512, 522, 532, 542).

In one embodiment, a fan, which is not shown in FIGS. 5A, 5B, 5C and 5D may be placed at the air inlet (513, 523, 533, 543) to force the air to flow through the reactor (511, 521, 531,541). The positions of the air outlet (512, 522, 532, 542) and the air inlet (513, 523, 533, 543) in the air purifier (510, 520, 530, 540) are arbitrary. The positions of the air outlet (512, 522, 532, 542) and the air inlet (513, 523, 533, 543) in the air purifier (510, 520, 530, 540) are determined by the design requirement, thus the positions of the air inlet (Air IN) and the air outlet (Air OUT) in the air purifier (510, 520, 530, 540) are not limited in this disclosure.

Figure 5A:
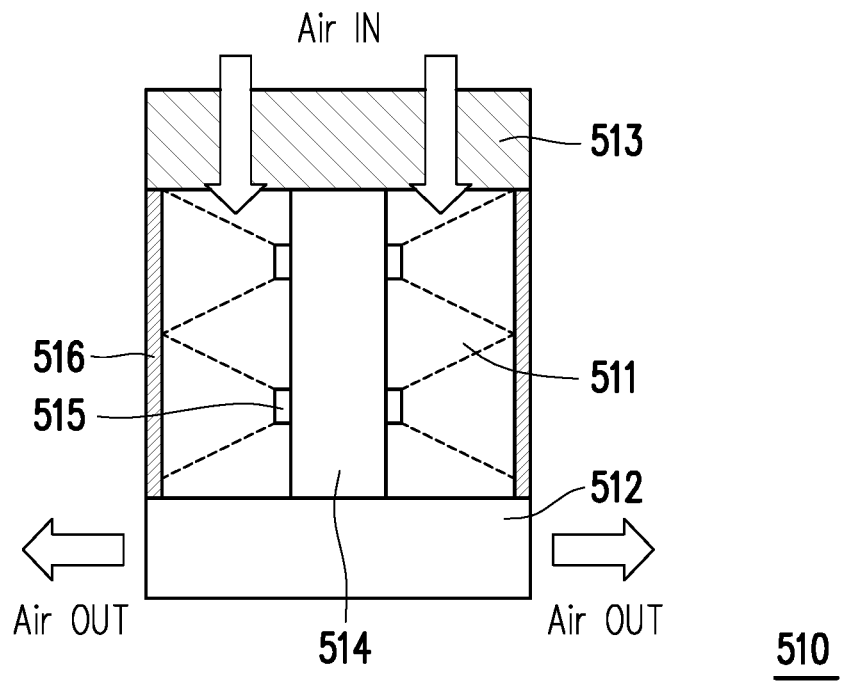
FIGS. 5A, 5B, 5C and 5D respectively illustrate the design structures of an air purifier according to an embodiment of the disclosure.

With reference to FIG. 5A, the column 514 is used for holding the light emitting elements 515 in the reactor 511. The column 514 disposed in the reactor 511 has N side walls. The value of N is determined to increase the number of light emitting elements 515 disposed on the N side walls of the column 514.

The light emitting elements 515 are disposed on the N side walls of the column 514. Each of the light emitting elements 515 emits light with an emitting angle of θ.

The emitting angle of the light emitting elements 515 in the column 514 with N side walls is determined as θ*N>360°.

In this embodiment, the light emitting elements 515 disposed on the column 514 are used for the photocatalytic oxidation process in the air purifier 510. In other words, the light emitting elements 515 emit light in the outward direction towards an inner side wall 516 of the reactor 511. The inner side wall 516 of the reactor 511 is coated with a photocatalyst to increase the total illuminated area during photocatalytic oxidation in the reactor 511. The light emitting elements 515 may irradiate the photocatalyst coated on the inner side wall 516 of the reactor 511 during air purification.

Figure 5B:
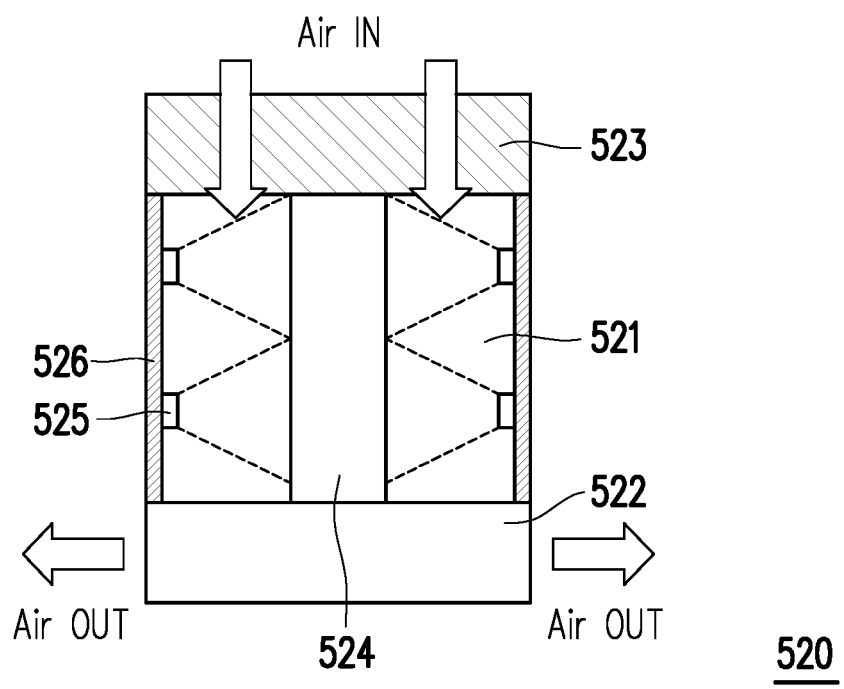

Referring to FIG. 5B, a sidewall of the column 524 is coated with a photocatalyst to increase the total illuminated area during photocatalytic oxidation in the reactor 521.

In this embodiment, the light emitting elements 525 disposed on the inner side wall 526 of the reactor 521 are used for the photocatalytic oxidation process in the air purifier 520. In other words, the light emitting elements 525 emit light in the inward direction towards the sidewall of the column 524 in the reactor 521. The light emitting elements 525 emit light to the photocatalyst coated on the sidewall of the column 524 to perform photocatalytic oxidation. The inner side wall 526 of the reactor 521 may be coated with a reflective material to reflect the light emitted from the light emitting elements 525. The reflective material on the inner side wall 526 of the reactor 521 is used to retain the light illuminated from the light emitting elements 525 in the reactor 521 during the photocatalytic oxidation, thus the light emitted by the light emitting elements 525 are maintained in the reactor 521 during air purification process, thereby increasing efficiency of air purification in the air purifier 520.

Figure 5C:
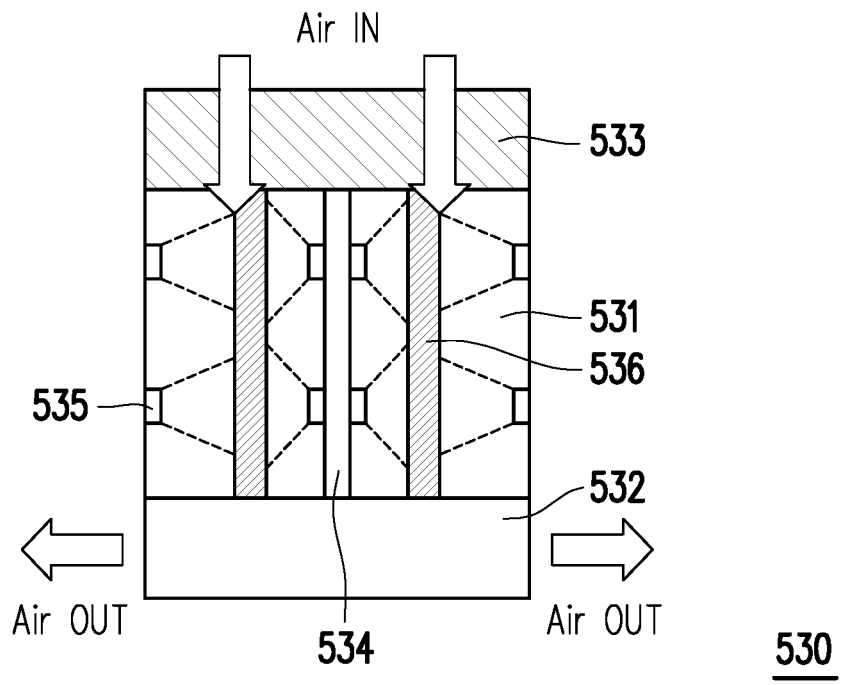

Referring to FIG. 5C, the light emitting elements 535 are not only disposed on the column 534 but also disposed on an inner side wall of the reactor 531.

In this embodiment, the purifier 530 further includes an air guider 536. The air guider 536 is in cylinder shape to guide the air to flow from the top to the bottom of the air purifier 540. A photocatalyst is coated on the outer side wall of the air guider 536. The light emitting elements 535 are placed on the inner side wall of the reactor 531 and on the column 534 emit light to the photocatalyst on the outer side wall of the air guider 536 to perform photocatalytic oxidation.

In some embodiments, a photocatalyst is coated on the inner side wall of the air guider 536.

The light emitting element 535 placed on the column 534 emit light to the photocatalyst on the inner side wall of the air guider 536 to perform photocatalytic oxidation. In other words, the light emitting elements 535 placed on the column emit light in the outward direction towards the air guider 536.

In some embodiments, the inner side wall of the reactor 531 is coated with a reflective material to reflect the light emitting from the light emitting elements 535 and thus to retain the light illuminated from the light emitting elements 535 in the reactor 530. In some embodiment, the column 534 can be coated with a reflective material to reflect the light emitting from the light emitting elements 535 and thus, to retain the light illuminated from the light emitting elements 535 in the reactor 530.

In some embodiments, the column 534, the air guider 536 and the side wall of the reactor 531 are concentric circles viewed from one end of the reactor 530. The column 534, the air guider 536 and the side wall of the reactor 531 are coaxial. That means the column 534, the air guider 536 and the side wall of the reactor 531 are centered on the same axis.

Figure 5D:
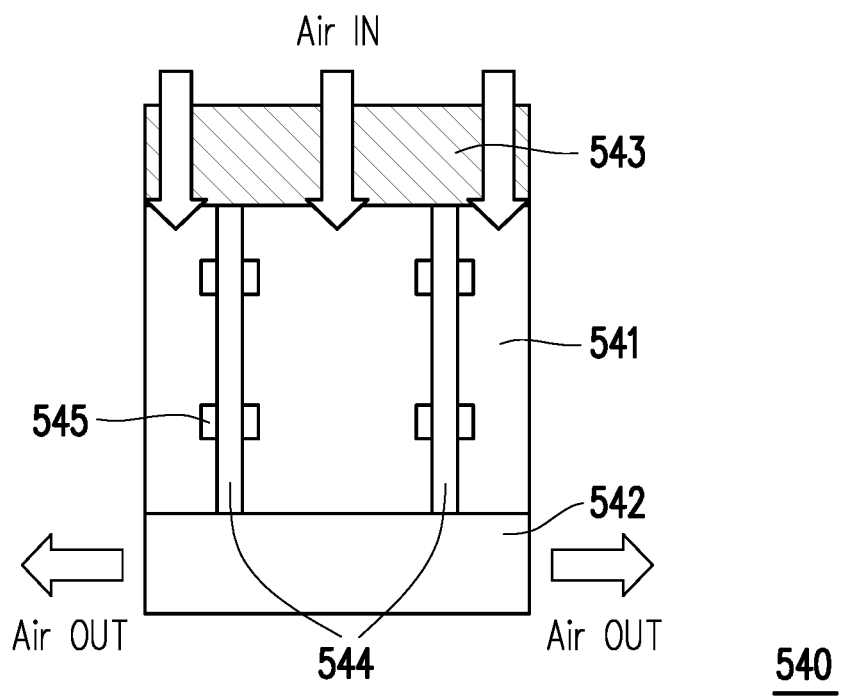

Referring to FIG. 5D, the reactor 540 includes a plurality of columns 544. Each of the plurality of columns 544 has N side walls. The value of N is determined to increase the number of light emitting elements 545 disposed in the N side walls of the column 544.

In one embodiment, the number of the columns 544 in the reactor 541 is 2. The positions of columns 544 in the reactor 541 are placed at the equal distance from the reactor 541.

In some embodiments, the number of columns 544 in the reactor 541 is greater than 2. In other words, the number of columns 544 in this embodiment is at least 2. Thus, the number of columns 544 in the reactor 541 is not limited in this disclosure.

In some embodiments, the positions of the columns 544 are placed in middle of the reactor 541.

In some embodiments, the distance between the columns 544 are equal. Thus, the columns 544 are in equal distance with the reactor 541.

In some embodiments, the distance between the column 544 are not at equal distance, and are determined by the design requirement, thus the positions of the columns 544 in the reactor 541 is not limited herein.

By using at least two columns 544 in the reactor 541, thereby increasing number of light emitting elements 545 in each of the columns 544 during photocatalytic oxidation in the air purifier 540.

Figure 6A:
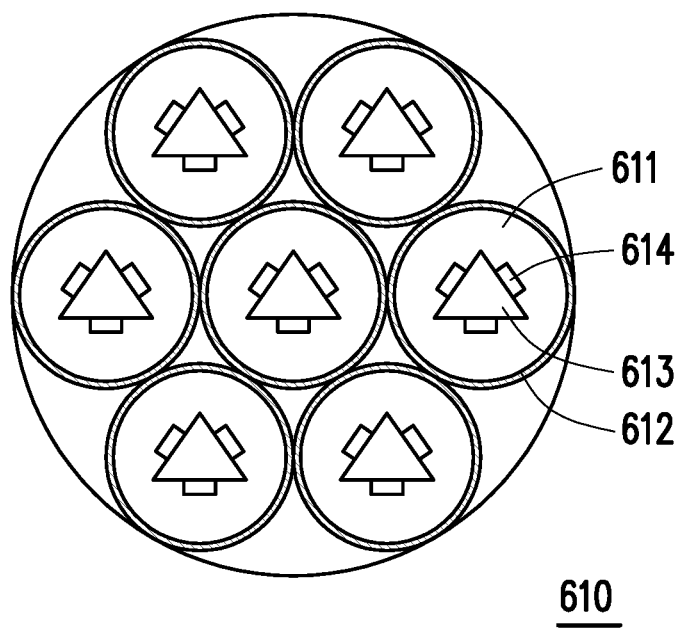
FIGS. 6A, 6B and 6C respectively illustrate an arrangement of a plurality of reactors in an air duct system according to an embodiment of the disclosure.
Figure 6B:
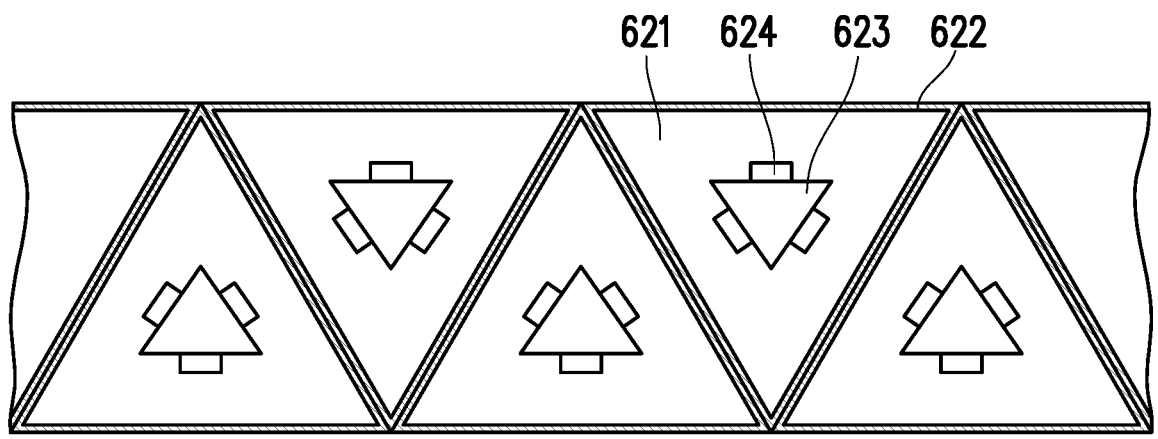
Figure 6C:
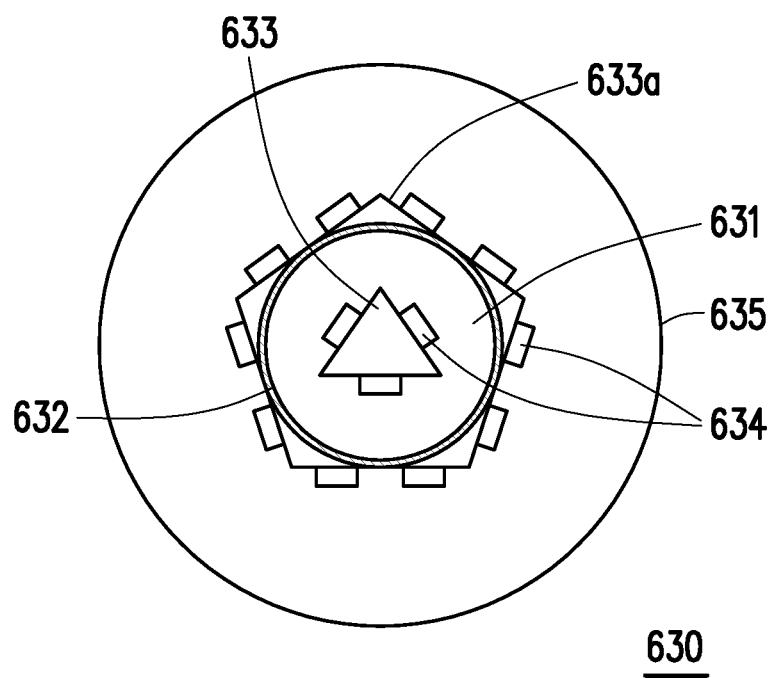

FIGS. 6A, 6B and 6C respectively illustrate the design arrangement of a plurality of reactors in an air duct system according to an embodiment of the disclosure.

With reference to FIGS. 6A and 6B, the air duct system (610, 620) includes a plurality of reactors (611, 621). Each of the reactors (611, 621) includes an inner side wall (612, 622). The inner side wall (612, 622) of the reactors are coated with a photocatalyst. The reactors (611, 621) in the air duct system (610, 620) are applicable to afore-mentioned embodiments in FIGS. 1-5, thus the type of reactors (611, 621) used in the air duct system (610, 620) is not limited in this disclosure.

With reference to FIG. 6A, the reactors 611 in the air duct system 610 are a circular or a cylindrical shape. Each of the reactors 611 includes a column 613 and a plurality of light emitting elements 614. The column 613 is used for holding the light emitting elements 614. The column 613 disposed in the reactors 611 has a N side walls.

In this embodiment, the value of N is 3, by which the number of light emitting elements 614 disposed on each side walls of the column 613 may be increased.

In this embodiment, the air duct system 610 is a circular or a cylindrical shape.

In some embodiments, the air duct system 610 may be a rectangle, a triangle, a pentagon, a hexagon and so on, thus the shape of air duct system 610 is not limited in this disclosure.

The reactors 611 are arranged as a honeycomb pattern in the air duct system 610. In detail, each of the reactors 611 are surrounded by six reactors 611 to form a honey comb structure. Based on this arrangement, the number of reactors 611 placed in the air duct system 610 is increased.

With reference to FIG. 6B, the reactors 621 in the air duct system 620 are with a triangular shape. Each of the reactors 621 includes a column 623 and a plurality of light emitting elements 624. The column 623 is used for holding the light emitting elements 624. The columns 623 are disposed in the reactors 621 has N side walls.

In this embodiment, the value of N is 3, by which the number of light emitting elements light emitting elements 624 disposed on each side walls of the columns 623 may be increased.

In this embodiment, the air duct system 620 is a rectangular shape.

The reactors 621 are arranged in a zig zag pattern in the air duct system 620. In other words, one inverted triangular reactor 621 is placed between two triangular reactors 621 forms the rectangular shape in the air duct system 620. Based on this arrangement, the number of reactors 621 placed in the air duct system 620 is increased.

With reference to FIG. 6C, the air duct system 630 includes a reactor 631. The reactor 631 further includes an inner side wall 632, a column 633 and a plurality of light emitting elements 634. The column 633 is used for holding the light emitting elements 634. The column 633 is disposed in the reactor 631 has N side walls.

In one embodiment, the value of N is 3, by which the number of light emitting elements 634 disposed on the each side walls of the columns 633 may be increased.

The air duct system 630 further includes a column 633a. The reactor 631 is surrounded by the column 633a. The column 633a is in a pentagonal shape and comprises M side walls. The value of M is 5 to increase the number of light emitting elements 634 disposed on the each side walls of the column 633a. The light emitting elements 634 are disposed on the outer sidewall of the column 633a.

The light emitting elements 634 are disposed on the M side walls of the column 633a. The light emitting elements 634 are disposed on the outer side walls of the column 633a. Each of the light emitting elements 634 emit light with an emitting angle of $\theta$. The emitting angle of the light emitting elements 634 on the column 633a with M side walls is determined as $\theta*M>360°$.

The photocatalyst is coated on the inner side wall 632 of the reactor 631 and the inner side wall 635 of the air duct system 630. The light emitting elements 634 disposed on the outer side sidewall of the column 633a emit light to the photocatalyst on the inner side wall 635 of the air duct system 630 to perform photocatalytic oxidation.

By using the photocatalyst coated on the inner side wall 632 of the reactor 631 and the inner side wall 635 of the air duct system 630, the total catalyst surface area is increased during photocatalytic oxidation in the air duct system 630.

In some embodiment, the outer side sidewall of column 633a is coated with a reflective material to reflect the light emitting from the light emitting elements 634 and thus to retain the light illuminated from the light emitting elements 634 in the air duct system 630.

In some embodiment, the column 633 may be coated with a reflective material to reflect the light emitting from the light emitting elements 634 and thus to retain the light illuminated from the light emitting elements 634 in the reactor 631.

In some embodiment, the column 633, 633a and the inner sidewall 635 of the air duct system 630 are coaxial. The column 633, 633a, and the inner sidewall 635 of the air duct system 630 are all centered on the same axial.

Figure 7:
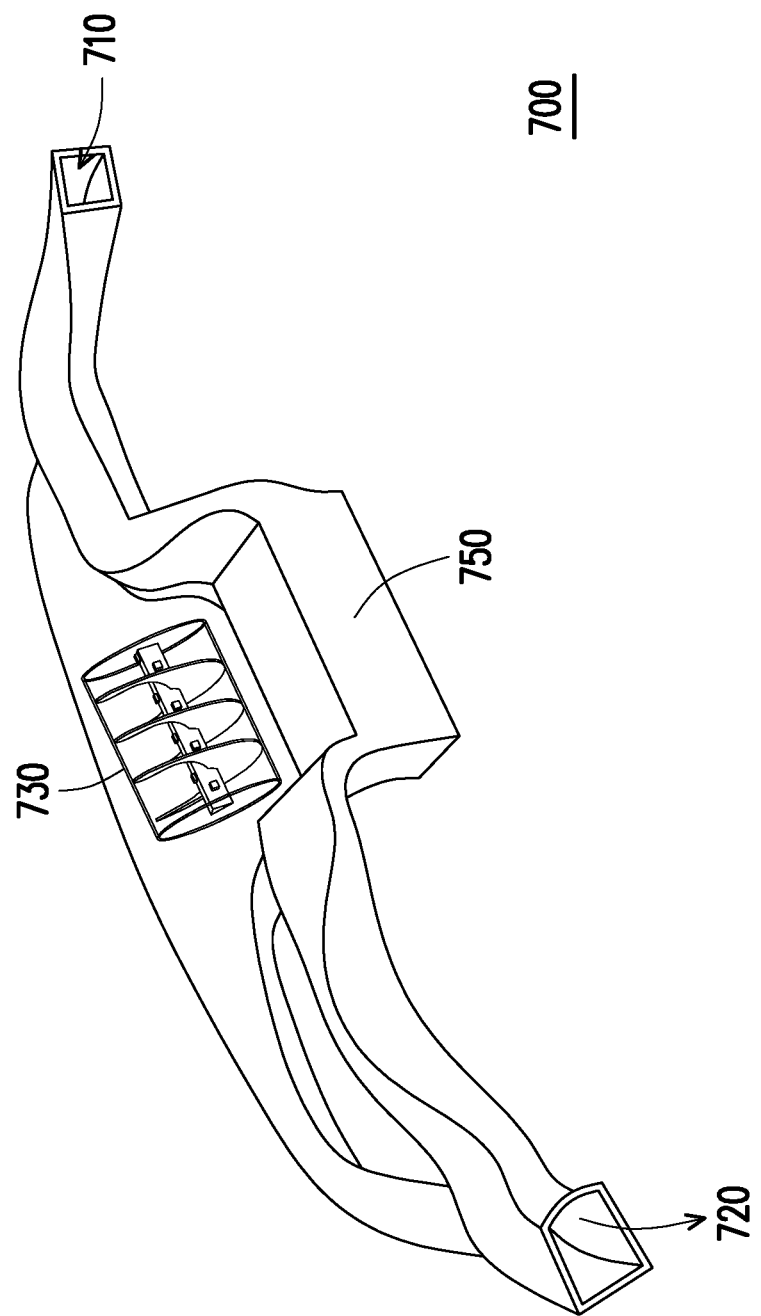
FIG. 7 illustrates an automobile air conditioner with an air purifier according to an embodiment of the disclosure.

FIG. 7 schematically shows an automobile air conditioner with an air purifier according to an embodiment of the disclosure. The automobile air conditioner 700 includes a vent chamber 750. The automobile air conditioner 700 further includes a heater and a cooler, which are the necessary components of the automobile air conditioner 700, thus the detail structure of the heater and the cooler are not shown in FIG. 7.

The heater is used to heat the air inside the vent chamber 750, and the cooler is used to cool the air inside the vent chamber 750. As the heater and the cooler are the conventional structures, the detailed schematic description is omitted herein.

The vent chamber 750 includes an air inlet 710, an air outlet 720 and an air purifier 730.

The air inlet 710 and the air outlet 720 are respectively similar to an air inlet 513 and an air outlet 512 with reference to FIG. 5A. The air flows into the air purifier 730 through the air inlet (Air IN) allows to perform the air purification process and purified air is obtain at the air outlet (Air OUT).

The air purifier 730 is applicable to the embodiments afore-mentioned in FIGS. 1-5, thus the detailed description of the air purifier 730 is omitted herein.

Figure 8:
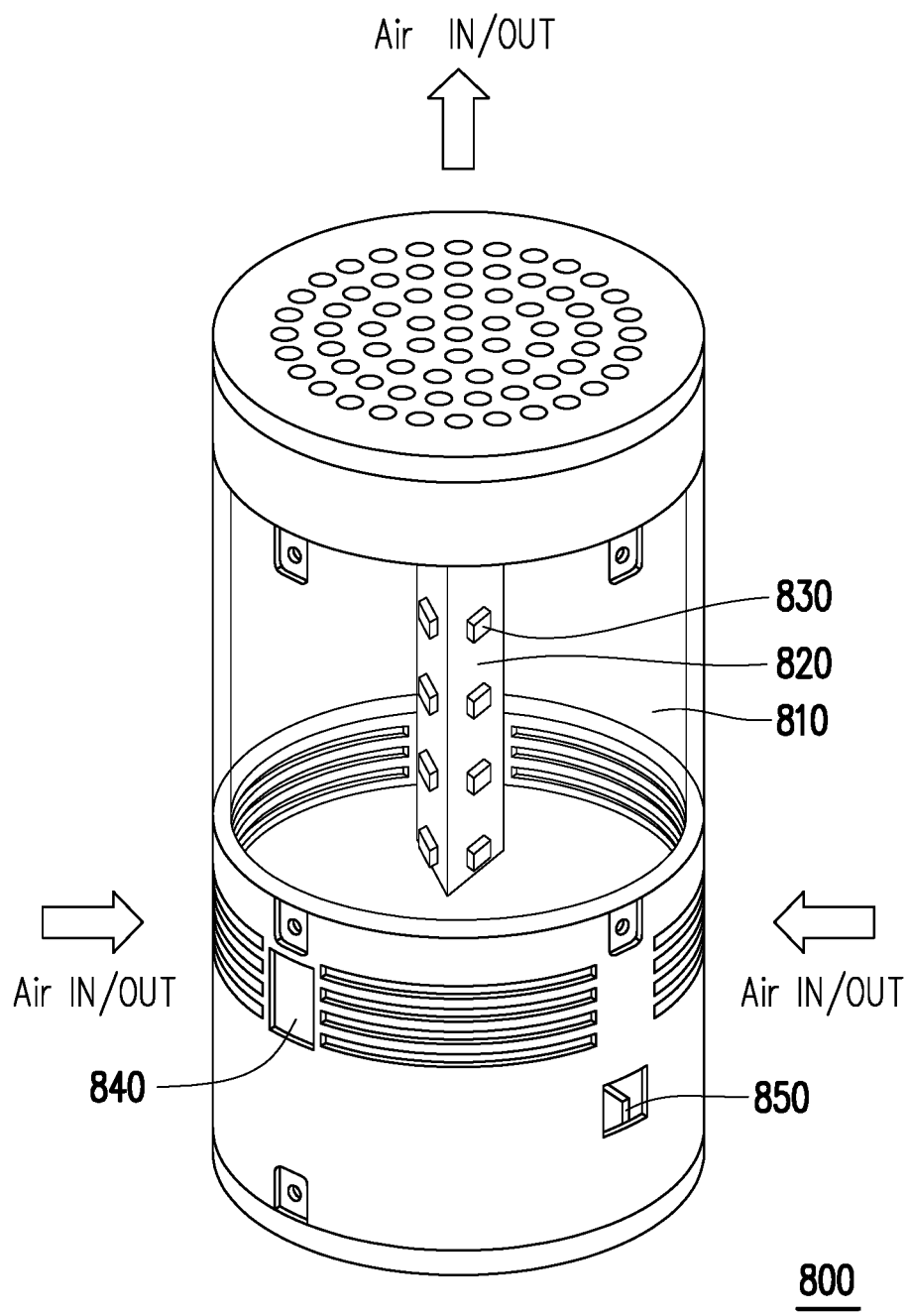
FIG. 8 illustrates an air purifier according to an embodiment of the disclosure.

FIG. 8 schematically shows an air purifier according to an embodiment of the disclosure. Referring to FIG. 8, an air purifier 800 of the embodiment includes a reactor 810, a column 820, a plurality of light emitting elements 830, a power switch 840 and a charging port 850. The reactor 810, the column 820, and the light emitting elements 830 are respectively similar to a reactor 110, a column 120 and a plurality of light emitting elements 130 with reference to FIG. 1, thus the detail description of structure and operations of the reactor 810, the column 820, and the light emitting elements 830 are omitted herein.

The reactor 810 has an air inlet (Air IN) at one end of the reactor 810, and an air outlet (Air OUT) at the other end of the reactor 810.

In the reactor, air flows into the air purifier 800 through the air inlet (Air IN) to perform air purification process and purified air is obtain by the air outlet (Air OUT).

In one embodiment, a fan, which is not shown in FIG. 8 is placed at the air inlet (Air IN) to force the air to flow through the reactor 810. The positions of the air inlet (Air IN) and the air outlet (Air OUT) in the air purifier 800 are arbitrary. The positions of the air inlet (Air IN) and the air outlet (Air OUT) in the air purifier 800 are determined by the design requirement, thus the positions of the air inlet (Air IN) and the air outlet (Air OUT) in the air purifier 800 are not limited in this disclosure.

The column 820 is used for holding the light emitting elements 830 in the reactor 810. The column 820 disposed in the reactor 810 has N side walls, and the value of N may be determined to increase the number of light emitting elements light emitting elements 820 disposed in the N side walls of the column 820.

The light emitting elements 830 are disposed on the N side walls of the column 820. Each of the light emitting elements 830 emit light with an emitting angle of $\theta$. The emitting angle of the light emitting elements 830 in the column 820 with N side walls is determined as $\theta*N>360°$.

The light emitting elements 830 disposed on the column 820 is used to perform photocatalytic oxidation in the air purifier 800.

The light emitting elements 830 may irradiate a photocatalyst during air purification process in the air purifier 800.

The power switch 830 is a mechanical switch or an electrical switch is used to turn on/off the air purifier 800.

In one embodiment, the power switch 830 is implemented as the mechanical switch which may be controlled by the user to turn on/off the air purifier 800.

In some embodiments, the power switch 830 is implemented as the electrical switch used to control by an external circuit or by user.

In some embodiments, the power switch 830 may turn on/off by the counter or timer to control the power switch 830 to turn on/off the air purifier 800, thus the implementation of power switch 830 in the air purifier 800 is not limited in this disclosure.

The charging port 850 is used to charge the battery, which is not shown in FIG. 8 in the air purifier 800.

In some embodiments, the charging port 850 is also a power supply to the air purifier 800 and charge the battery at the same time.

In some embodiments, the air purifier 800 may also operates with the direct power source provided from the power supply through the charging port 850.

In some embodiments, when the direct power supply is not available, the air purifier 800 is powered by the battery presented in the air purifier 800, thus the air purifier 800 is powered by battery or by the direct power supply provided through the charging port 850.

The operation and the structure of the air purifier 800 is similar to the air purifier 100 with reference to FIG. 1, thus the detailed descriptions are omitted herein.

Figure 9:
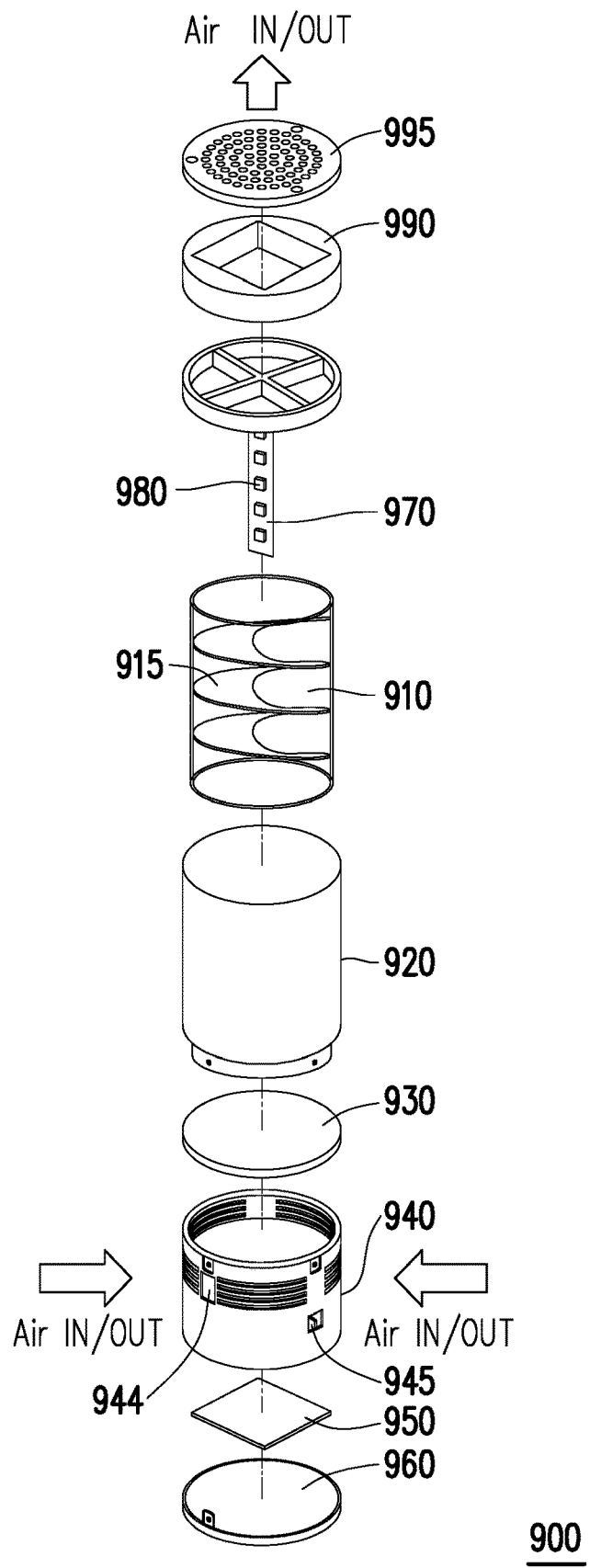
FIG. 9 illustrates an exploded view of an air purifier according to an embodiment of the disclosure.

FIG. 9 schematically shows an exploded view of an air purifier according to an embodiment of the disclosure. The air purifier 900 includes a reactor 910, an air guider 915, a reactor housing 920, a controller 930, an air inlet/outlet housing 940, a power switch 944, a charging port 945, a battery 950, a bottom cover 960, a column 970, a plurality of light emitting elements 980, a fan holder 990, and a top cover 995. The reactor 910, the column 970, and the light emitting elements 980 are respectively similar to the reactor 110, the column 120 and the light emitting elements 130 with reference to FIG. 1, thus the detail description of structure and operations of the reactor 910, the column 970, and the light emitting elements 980 are omitted herein.

The air guider 915 is disposed in the reactor 910. The air guider 915 may be a helical, a cylinder, a pentagonal, a hexagonal and/or disk shape and the shape of air guider 440 is determined by the design requirement, thus the shape of air guider 915 is not limited in the disclosure.

In some embodiments, the helical shape air guider 915 is preferred. The air guider 915 with the helical shape is used in the air purifier 900 is to increase residence time of the air with a VOCs during air purification process in the air purifier 900, thereby efficiency of air purification in the air purifier 900 is improved.

In some embodiments, a photocatalyst is coated on the inner side wall of the reactor 910 and surface of the air guider 915 to obtain the maximum irradiation on the photocatalyst in the air purifier 900, thus the presence of the photocatalyst in the air purifier 900 is not limited in the disclosure.

The light emitting elements 985 may irradiate a photocatalyst presented in the inner side wall of the reactor 910 and the air guider 915 during air purification.

The reactor housing 920 is the housing for the air purifier 900. The reactor housing 920 is used as a housing/cover for the reactor 910, a column 970 and the light emitting elements 880. The reactor housing 920 is a solid material and/or a transparent glass, thus the type of reactor housing 920 is not limited in this disclosure.

The controller 940, which is an electronic circuit board in the air purifier 900. The controller 940 is used to control the illumination intensity of the light emitting elements 880 disposed on the column 970.

The air inlet/air outlet housing 940 works as a housing for air inlet/air outlet of the air purifier 900. The air inlet/air outlet housing 940 is a solid material and/or a transparent glass, thus the type of air inlet/air outlet housing 940 is not limited in this disclosure.

The power switch 944 and the charging port 945 are respectively similar to a power switch 840 and a charging port 850 with reference to FIG. 8, thus the detail description of structure and operations of the power switch 944 and the charging port 945 are omitted herein.

The battery 950 is used to provide the power to the air purifier 900. The battery 950 is charged by the external power provided through the charging port 945. When the external power is not provided to the air purifier 900, the battery 950 will provide power to the air purifier 900.

The column 970 is used for holding the light emitting elements 980 in the reactor 910. The column 970 is disposed in the reactor 910 has N side walls.

It is noted that the placement of the column 980 in the air purifier 900 is in the top cover 995.

In some embodiments the placement of the column 980 in the air purifier, thus the positions of the columns in the air purifier 900 is not limited in this disclosure.

Based on the above, by choosing the number of N sidewalls of the column in the air purifier, total illuminated area of the air purifier is increased. In some embodiments, by choosing the helical structure guider, the residence time of the air during the air purification is improved, thereby increasing efficiency of the air purifier.

Figure 10:
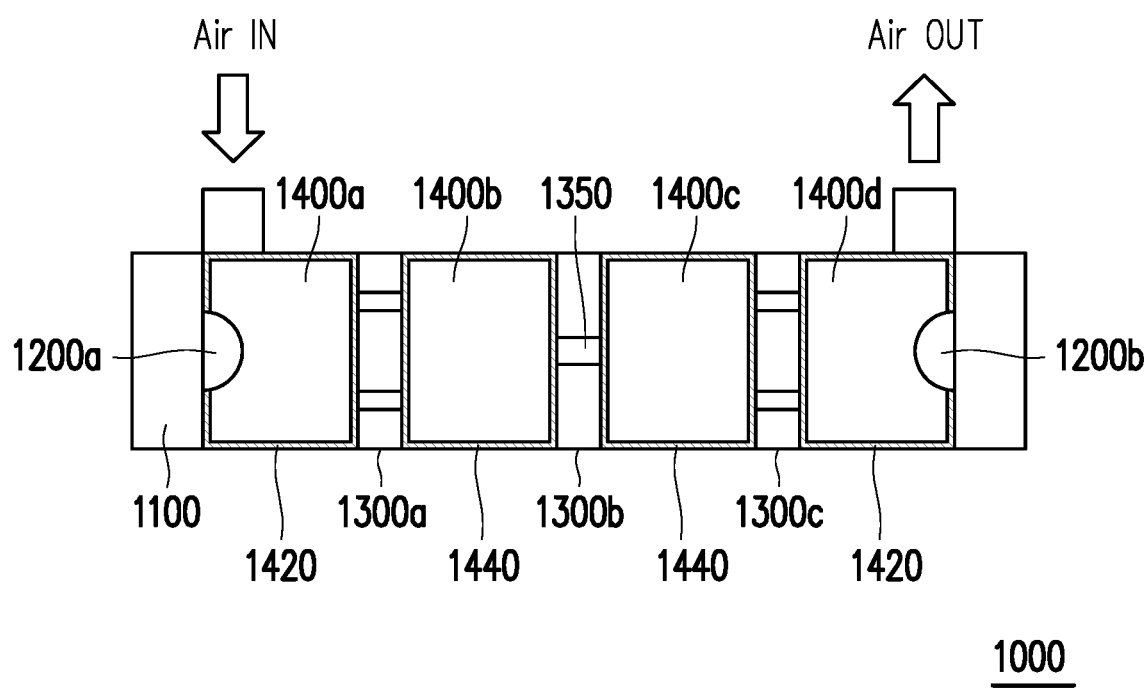
FIG. 10 illustrates an air purifier according to an embodiment of the disclosure.

FIG. 10 schematically shows an air purifier according to an embodiment of the disclosure. Referring to FIG. 10, an air purifier 1000 of the embodiment includes a reactor 1100, a plurality of light emitting elements (1200a, 1200b), and a plurality of transparent plates (1300a, 1300b, 1300c). The reactor 1100 and the light emitting elements (1200a, 1200b) are respectively similar to a reactor 110 and a plurality of light emitting elements 130 with reference to FIG. 1, thus the detail description of structure and operations of the reactor 1100 and the light emitting elements (1200a, 1200b) are omitted herein.

The reactor 1100 has an air inlet (Air IN) at one end of the reactor 1100, and an air outlet (Air Out) at the other end of the reactor 1100. In the reactor 1100, air flows into the air purifier 1000 through the air inlet (Air IN) to perform air purification process and purified air is obtain by the air outlet (Air Out).

In this embodiment, the reactor 1100 is a rectangular shape.

The light emitting elements (1200a, 1200b) are disposed on either side of the reactor 1100. In detail, one light emitting element 1200a is disposed at the air inlet (Air IN) and other light emitting element 1200b is disposed at the air outlet (Air OUT).

In some embodiments, the number of light emitting elements (1200a, 1200b) in the reactor 1100 is more than two, thus the number of light emitting elements (1200a, 1200b) in the reactor 1100 is not limited in this disclosure.

In some embodiments, the reactor 1100 may be a triangle, a square, a pentagon, a hexagon shape and so on, thus the shape of the reactor 1100 is not limited in this disclosure.

The transparent plates (1300a, 1300b, 1300c) are disposed in the reactor 1100.

In this embodiment, the number of transparent plates (1300a, 1300b, 1300c) in the reactor 1100 is 3.

The transparent plates (1300a, 1300b, 1300c) divides the reactor 1100 into a first chamber 1400a, a second chamber 1400b, a third chamber 1400c, and a fourth chamber 1400d.

The number of transparent plates (1300a, 1300b, 1300c) in the reactor 1100 is at least one, thus the number of transparent plates (1300a, 1300b, 1300c) in the reactor 1100 is not limited in this disclosure.

In detail, if the number of transparent plates (1300a, 1300b, 1300c) in the reactor 1100 is (N), and the number of chambers (1400a, 1400b, 1400c, 1400d) in the reactor 1100 is (N+1), thus the number of chambers (1400a, 1400b, 1400c, 1400d) is varied according to the number of transparent plates (1300a, 1300b, 1300c) disposed in the reactor 1100.

In one embodiment, the position of the transparent plates (1300a, 1300b, 1300c) are placed at an equal distance in the reactor 1100.

In some embodiments, the position of the transparent plates (1300a, 1300b, 1300c) are not at an equal distance, and are determined by the design requirement, thus the positions of transparent plates (1300a, 1300b, 1300c) in the reactor 1100 is not limited herein.

In one embodiment, the transparent plates (1300a, 1300b, 1300c) are disposed in the reactor 1100 has at least one hole 1450.

The air flows into the different chambers (1400a, 1400b, 1400c, 1400d) for air purification through the hole 1450 in the transparent plates (1300a, 1300b, 1300c).

In this embodiment, the number of holes 1450 in the transparent plates (1300a, 1300c) is two and the number of holes 1450 in the transparent plate 1300b is one.

In some embodiments, the number of holes 1450 in the transparent plates (1300a, 1300b, 1300c) are more than two, thus the number of holes 1450 in the transparent plates (1300a, 1300b, 1300c) are not limited thereto.

In one embodiment, the position of the holes 1450 are placed at an equal distance in the transparent plates (1300a, 1300b, 1300c).

In some embodiments, the position of the holes 1450 are not at an equal distance, and are determined by the design requirement, thus the positions of holes 1450 in the transparent plates (1300a, 1300b, 1300c) are not limited herein.

An inner sidewall of the chambers (1400a, 1400b, 1400c, 1400d) are coated with a plurality of photocatalyst layers (1420, 1440). The photocatalyst layers are divided into a first photocatalyst layer 1420 and a second photocatalyst layer 1440.

In one embodiment, the material of the first photocatalyst layer 1420 and the second photo catalyst layer 1440 are same.

In some embodiments, the material of the first photocatalyst layer 1420 and a second photocatalyst layer 1440 are different In this embodiment, the inner sidewalls of the first chamber 1400a and the fourth chamber 1400d are coated with the first photocatalyst layer 1420. Similarly, the inner sidewalls of the second chamber 1400b and the third chamber 1400c are coated with the second photocatalyst layer 1440.

The material of the first photocatalyst layer 1420 and the second photocatalyst layer 1440 may be titanium dioxide, zinc oxide, stannic oxide, zirconium oxide, ferric oxide, cadmium sulfide, cadmium selenide, tungsten trioxide, molybdenum trioxide, vanadium pentoxide, tin oxide, and/or combinations of the different photocatalyst, thus the material of the photocatalyst layers (1420,1440) are not limited in this disclosure.

The material of the photocatalyst layers (1420,1440) are chosen according to the type of the light emitting elements (1200a, 1200b) in the reactor 1100. Based on the type of the photocatalyst layers (1420,1440) and type of the light emitting elements (1200a, 1200b), the photocatalytic oxidation time during air purification in the reactor 1100 is varied.

Based on the number of transparent plates (1300a, 1300b, 1300c), the number of light emitting elements (1200a, 1200b), the number of holes 1450, and the type of photocatalyst layers (1420,1440) used in the reactor 1100, the efficiency of air purification in the air purifier 1000 is improved.

No element, act, or instruction used in the detailed description of disclosed embodiments of the present application should be construed as absolutely critical or essential to the present disclosure unless explicitly described as such. Also, as used herein, each of the indefinite articles "a" and "an" could include more than one item. If only one item is intended, the terms "a single" or similar languages would be used. Furthermore, the terms "any of" followed by a listing of a plurality of items and/or a plurality of categories of items, as used herein, are intended to include "any of", "any combination of", "any multiple of", and/or "any combination of multiples of the items and/or the categories of items, individually or in conjunction with other items and/or other categories of items. Further, as used herein, the term "set" is intended to include any number of items, including zero. Further, as used herein, the term "number" is intended to include any number, including zero.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. An air purifier, comprising:
   a reactor comprising an air inlet and an air outlet;
   a column disposed in the reactor, wherein the column has a N side walls;
   an air guider disposed on the column;
   a photocatalyst disposed in the reactor; and
   a plurality of light emitting elements disposed on the N side walls of the column configured to irradiate on the photocatalyst, and each of the light emitting elements has an emitting angle of θ, wherein θ*N>360°.

2. The air purifier of claim 1, wherein the plurality of light emitting elements is an ultraviolet LED, a visible light or an infrared LED.

3. The air purifier of claim 1, wherein a ratio of a distance between two adjacent light emitting elements to a radius of the reactor is 3:5.

4. The air purifier of claim 1, wherein the shape of the air guider is helical.

5. The air purifier of claim 1, wherein a distance between the plurality of two adjacent light emitting elements are equal to a pitch of the air guider.

6. The air purifier of claim 1, wherein a distance between each of the light emitting elements disposed on the column to each side of the air guider disposed on the column is equal to half of a pitch of the air guider.

7. The air purifier of claim 1, wherein the air guider is coated with the photocatalyst.

8. The air purifier of claim 1, wherein an inner wall of the reactor is coated with the photocatalyst.

9. The air purifier of claim 1, wherein the air guider is configured to rotate along an axis of the column.

10. An automobile air conditioner, comprising a vent chamber, wherein the vent chamber comprises an air inlet and an air outlet;
   a reactor configured to purify air in the automobile air conditioner;
   a column disposed in the reactor, wherein the column has a N side walls;

an air guider disposed on the column;

a photocatalyst disposed in the reactor; and a plurality of light emitting elements disposed on the N side walls of the column configured to irradiate on the photocatalyst and each of the light emitting elements has an emitting angle of θ, wherein θ*N>360 °.

11. The automobile air conditioner of claim 10, wherein the plurality of light emitting elements is an ultraviolet LED, a visible light or an infrared LED.

12. The automobile air conditioner of claim 10, wherein a ratio of a distance between two adjacent light emitting elements to a radius of the reactor is 3:5.

13. The automobile air conditioner of claim 10, wherein the shape of the air guider is helical.

14. The automobile air conditioner of claim 10, wherein a distance between the plurality of two adjacent light emitting elements are equal to a pitch of the air guider.

15. The automobile air conditioner of claim 10, wherein a distance between each of the light emitting elements disposed on the column to each side of the air guider disposed on the column is equal to half of a pitch of the air guider.

16. The automobile air conditioner of claim 10, wherein the air guider is coated with the photocatalyst.

17. The automobile air conditioner of claim 10, wherein an inner wall of the reactor is coated with the photocatalyst.

18. The automobile air conditioner of claim 10, wherein the air guider is configured to rotate along an axis of the column.

19. An air purifier, comprising:

a reactor comprising an air inlet and an air outlet;

a plurality of columns disposed in the reactor, wherein each of the plurality of columns has a N side walls;

a plurality of light emitting elements disposed on the N side walls of the plurality of columns configured to irradiate on a photocatalyst, and each of the light emitting elements has an emitting angle of θ, wherein 0*N>360°.

20. The air purifier of claim 19, wherein an air guider disposed on each of the plurality of the columns, and the air guider is coated with the photocatalyst.

* * * * *